United States Patent [19]

Babaian-Kibala et al.

[11] Patent Number: 5,503,006
[45] Date of Patent: *Apr. 2, 1996

[54] HIGH TEMPERATURE CORROSION SIMULATOR

[75] Inventors: Elizabeth Babaian-Kibala, Fulshear; Joe S. Walker, Missouri City; John G. Hyatt; Sam Ferguson, both of Sugar Land, all of Tex.

[73] Assignee: Nalco Chemical Company, Naperville, Ill.

[*] Notice: The term of this patent shall not extend beyond the expiration date of Pat. No. 5,425,267.

[21] Appl. No.: 147,745

[22] Filed: Nov. 4, 1993

Related U.S. Application Data

[63] Continuation-in-part of Ser. No. 114,479, Aug. 31, 1993, Pat. No. 5,425,267.

[51] Int. Cl.$^6$ ................................................. G01N 17/00
[52] U.S. Cl. .................................. 73/86; 73/865.6
[58] Field of Search ........................ 422/53; 73/86, 73/19.01, 865.6

[56] References Cited

U.S. PATENT DOCUMENTS

| | | | |
|---|---|---|---|
| 2,664,744 | 1/1954 | Bilhartz et al. | 73/86 |
| 4,056,968 | 11/1977 | Winslow, Jr. | 73/19 |
| 4,065,373 | 12/1977 | Martin et al. | 204/195 |
| 4,335,072 | 6/1982 | Barnett et al. | 422/53 |
| 4,416,996 | 11/1983 | von Klock et al. | 436/6 |
| 4,599,217 | 7/1986 | Winston et al. | 422/53 |
| 4,683,035 | 7/1987 | Hunt et al. | 204/1 T |
| 4,686,854 | 8/1987 | Herman | 73/86 |
| 4,711,131 | 8/1987 | Hopkins | 73/799 |
| 5,254,310 | 10/1993 | Bressan | 422/53 |
| 5,260,218 | 11/1993 | Garde | 422/53 |
| 5,425,267 | 6/1995 | Herrmann et al. | 73/86 |

OTHER PUBLICATIONS

A. Wachter and R. S. Treseder; Corrosion Testing; Evaluation of Metals for Process Equipment; Shell Development Company, Emeryville, California; Jun. 1947.

*Primary Examiner*—Richard Chilcot
*Assistant Examiner*—Max Noori
*Attorney, Agent, or Firm*—Robert A. Miller; James J. Drake; Patricia A. Charlier

[57] ABSTRACT

An apparatus of provided for simulating corrosion activity of a high temperature liquid stream. The apparatus includes a canister in which is positioned a plug, occupying part of the internal volume of the canister. A stream of high temperature liquid enters the canister through an inlet, flows around the plug, and exits the canister through an outlet. The volume and configuration of the plug may be varied to simulate corrosion activity under various flow regimes. Probes may be placed in the liquid stream to detect corrosion activity and temperature. Several canisters may be arranged in series, and corrosion activity may be simulated in each canister simultaneously to determine effects of various parameters such as liquid impingement, velocity, and temperature on corrosion activity.

15 Claims, 4 Drawing Sheets

HIGH TEMPERATURE CORROSION SIMULATOR

This application is a continuation-in-part of Ser. No. 08/114,479 entitled "Corrosion Simulator and Method for Simulating Corrosion Activity of a Process Stream" by William B. Herrmann, Daniel S. Mull, John G. Hyatt, Paul Fearnside and Russell C. Strong, filed on Aug. 31, 1993, issued Jun. 10, 1995, U.S. Pat. No. 5,425,267.

BACKGROUND OF THE INVENTION

1. Field of the Invention

The present invention relates generally to an apparatus for simulating corrosion activity and, more particularly, to an apparatus for simulating corrosion activity of high temperature liquid streams.

2. Description of Related Art

Corrosion is considered a serious problem in a great number of industrial settings. In the chemical industry corrosion activity in process machinery and lines limits equipment life and can threaten the reliability of industrial installations. Corrosive materials in process fluids can result in excessive downtime for equipment repair as well as high maintenance costs related to correcting the effects of corrosion. Control of corrosion in industrial settings can be carried out effectively only if the corrosion activity of process fluids can be detected or modelled accurately.

Once information on corrosion activity is collected, several preventive and remedial measures are available to limit the degradation caused to process equipment. The design of an effective corrosion control program may include strategic injection of corrosion inhibitors, adjustment of process parameters such as flow rates, temperatures and chemical compositions, and specification of particular equipment layouts or metallurgical upgrades designed to minimize the effects of corrosion. However, an effective corrosion control program typically begins with information on the corrosion activity anticipated or actually occurring in the particular installation.

Corrosion in process machinery and on the process side of refinery equipment is most often due either to the activity of aqueous phase corrosive materials generated during condensing of process vapors, or to the direct effect of corrosive liquids present in the installation. In the case of corrosion caused by an aqueous phase, corrosion activity generally takes place on the metal surfaces of the equipment and particularly on the internal surfaces of condensing and heat exchange units where condensation initiates. On the other hand, the corrosion activity of process fluids in the liquid phase is more difficult to anticipate. Of particular importance in many chemical process installations is the corrosion activity of high temperature liquids. In the following discussion of the invention, the term "high temperature" will be utilized to describe liquids whose temperature is in excess of about 300° F. The rate and location of the corrosion activity of high temperature liquid streams often depends on such factors as temperature, flow rates, impingement forces, velocities, the metallurgy of process and transport equipment and lines, and the chemical composition of the liquid stream.

A number of devices and methods are known for the detection and simulation of corrosion activity of vapors and vapor condensates. Such devices generally divert a vapor phase slip stream from process machinery in which corrosion activity is to be detected or modelled and circulate the slip stream through a cooled container. Corrosion activity is detected by corrosion probes or weight loss coupons situated in the slip stream. However, such systems are generally not suitable for simulating corrosion activity of high temperature liquid streams due to differences in the parameters associated with corrosion in the two cases. Most significantly, corrosion activity of high temperature liquids is not dependent on the condensation in heat exchange units that such systems are designed to model.

Several techniques have been used for the detection of corrosion activity of process fluids in the liquid phase. One such technique relies on the insertion of corrosion probes or weight loss coupons in the process machinery itself. However, the pressures and temperatures often associated with chemical processes severely limit the opportunity to place and remove such probes or coupons, thus limiting access to information on corrosion activity that they are designed to provide. In addition, the location of the most severe corrosion in an industrial installation will often change over time, making the most judicious placement of probes and coupons difficult to determine.

Other known techniques for determining corrosion activity of liquid phase process streams rely on sampling of the process liquids. Samples are generally taken either from the process machinery, such as from bleed valves located in pump around circuits. Pump around circuits are loops in process machinery for diverting and later reinjecting a portion of the process stream, often for reasons related to temperature control. Once collected, such samples can be subjected to chemical testing for corrosive agents or for corrosion by-products correlated to corrosion activity in the machinery. However, the sensitivity of such techniques is often poor. In addition, sample testing is often time consuming and can thus impose considerable delay between the time of sampling and the reception of analytical results of corrosion tests. Alternatively, samples have been used to gain information on corrosion activity by placing the liquid sample in contact with corrosion coupons representative of process machinery metallurgy. A major shortfall of this technique is its inability to model the dynamic corrosive activity of the liquid stream present in the actual installation. Also, corrosive materials present in many process streams degrade over time, making simulations by exposure of corrosion coupons to a specific liquid sample non-representative of the corrosion activity occurring in process machinery that is constantly exposed to a fresh stream of high temperature liquid.

The present invention is directed to overcoming or minimizing the drawbacks of the existing techniques set forth above.

SUMMARY OF THE INVENTION

In accordance with one aspect of the invention, there is provided an apparatus for simulating corrosion activity of a high temperature liquid. The apparatus includes a canister having an inlet for receiving a stream of high temperature liquid and an outlet for discharging the corrosive liquid stream. The canister is also provided with a plug port and has a predetermined internal volume. The apparatus further includes a plug positioned within the canister through the plug port. The plug partially occupies the internal volume of the canister to alter flow characteristics of the stream of liquid through the canister.

In accordance with another aspect of the present invention, there is provided an apparatus for simulating corrosion activity of a high temperature liquid that includes a plurality of serially coupled modular canisters, each canister having an inlet and an outlet for a high temperature corrosive liquid stream, a plug port and a predetermined internal volume. A plurality of plugs are provided, with one plug being positioned within each of the canisters through the respective plug port to alter the flow characteristics of the stream of liquid through the respective canister. The inlet of the first of the serially coupled canisters is coupled to a source of high temperature corrosive liquid and the outlet of the last of the canisters is coupled to a discharge point such that a sufficient pressure drop is established across the apparatus to assure movement of corrosive liquid through the canisters.

BRIEF DESCRIPTION OF THE DRAWINGS

The present invention will become more fully understood from the following detailed description, taken in conjunction with the accompanying drawings, wherein like reference numerals refer to like pans, in which.

While the invention is susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents and alternatives falling within the spirit and scope of the invention as defined by the appended claims.

DESCRIPTION OF THE PREFERRED EMBODIMENTS

Figure 1:
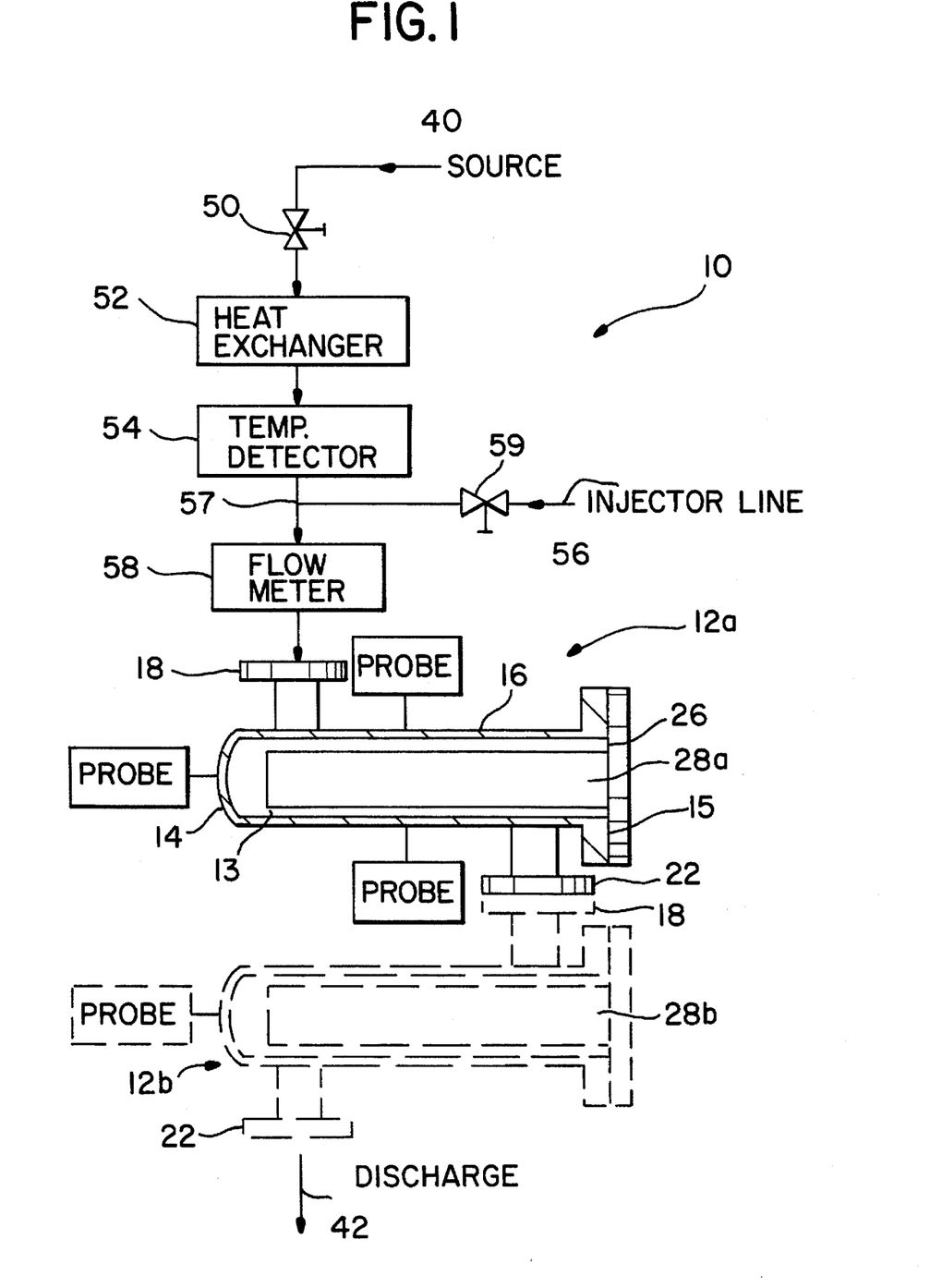
FIG. 1 is a diagrammatic view of a high temperature corrosion simulator in accordance with the invention illustrating the flow of high temperature liquid through certain of the elements included in a typical installation of the corrosion simulator.
Figure 2:
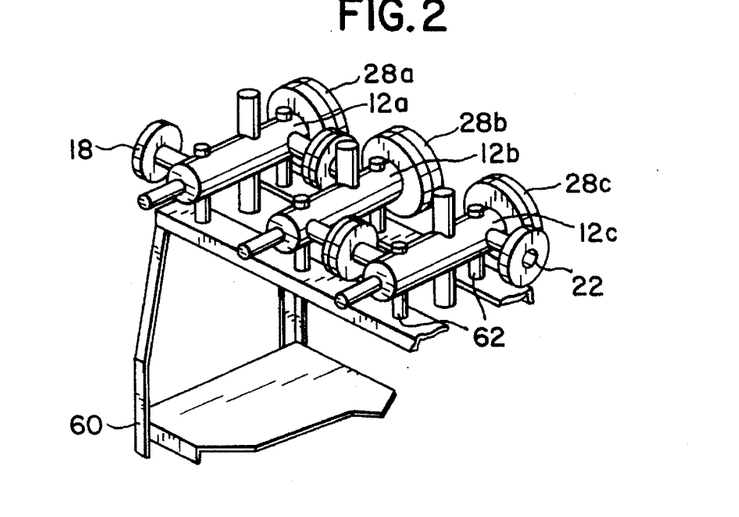
FIG. 2 is a perspective view of a series of modular canisters according to the invention, mounted on a supporting rack.

Turning now to the drawings and referring initially to FIG. 1, a high temperature corrosion simulator is illustrated diagrammatically and designated generally by the reference numeral 10. In a preferred form, the corrosion simulator 10 comprises a canister 12 having a predetermined internal volume 13, an inlet 18 for receiving a stream of high temperature corrosive liquid, an outlet 22 for discharging the liquid stream, and a plug port 26. Throughout the following description, reference will be made to the canister 12 and to a plurality of canisters 12a, 12b, 12c interconnected in series as depicted in FIGS. 1 and 2. Although the simulator 10 as illustrated in FIGS. 1 and 2 includes two and three canisters, the number of canisters actually utilized in a particular simulation application will vary depending upon the simulation requirements and a typical simulation may require a single canister or seven or more canisters coupled in series. It should be borne in mind throughout the following discussion that all canisters 12, 12a, 12b, 12c to which reference is made are substantially similar and contain identical pans, unless otherwise indicated.

The canister 12 is preferably cylindrical in shape, having a first end 14 and a second end 15 joined by a cylindrical lateral wall 16. As depicted in FIG. 1, the inlet 18 is located in the lateral wall 16 adjacent to the first end 14, and the outlet 22 is located in the lateral wall 16 adjacent to the second end 15. This arrangement of the inlet 18 and outlet 22 causes the liquid stream entering the inlet 18 to circulate through the canister 12 before exiting through the outlet 22. As will become apparent in the following discussion, because the canister 12 is preferably of a modular construction, the port designated as the inlet 18 in the present description can alternatively serve as the outlet 22 and vice versa, simply by inverting the modular canister 12. This design offers the significant advantage of facilitating the coupling of a plurality of canisters 12a, 12b, 12c in series, with the inlet 18 of one canister 12b taking flow from the outlet 22 of the canister 12a immediately preceding it in the series. While the preferred configuration of the simulator 10 where several canisters 12a, 12b, 12c are employed is this series arrangement, several canisters 12a, 12b, 12c may alternatively be coupled in a parallel arrangement, each taking flow from a header or manifold (not shown), as will be appreciated by those skilled in the art.

The canister 12 is preferably made of a material of sufficient mechanical strength to withstand the pressures and temperatures likely to arise in the simulation intended. In addition, at least those portions of the canister wetted by the high temperature liquid stream should be made of a material sufficiently resistant to corrosion to ensure the canister a reasonably long useful life. Metal alloys having a molybdenum content in excess of 3% are generally preferred. Metals satisfying this criterion include 317 stainless steel, Chlorimet 3, Hastelloy B, Hastelloy C, and 20Mo-6. It will be appreciated that the materials utilized in different applications may vary depending upon the specific parameters of the simulations intended and upon the relative corrosive ability of the liquid stream being tested.

Figure 4:
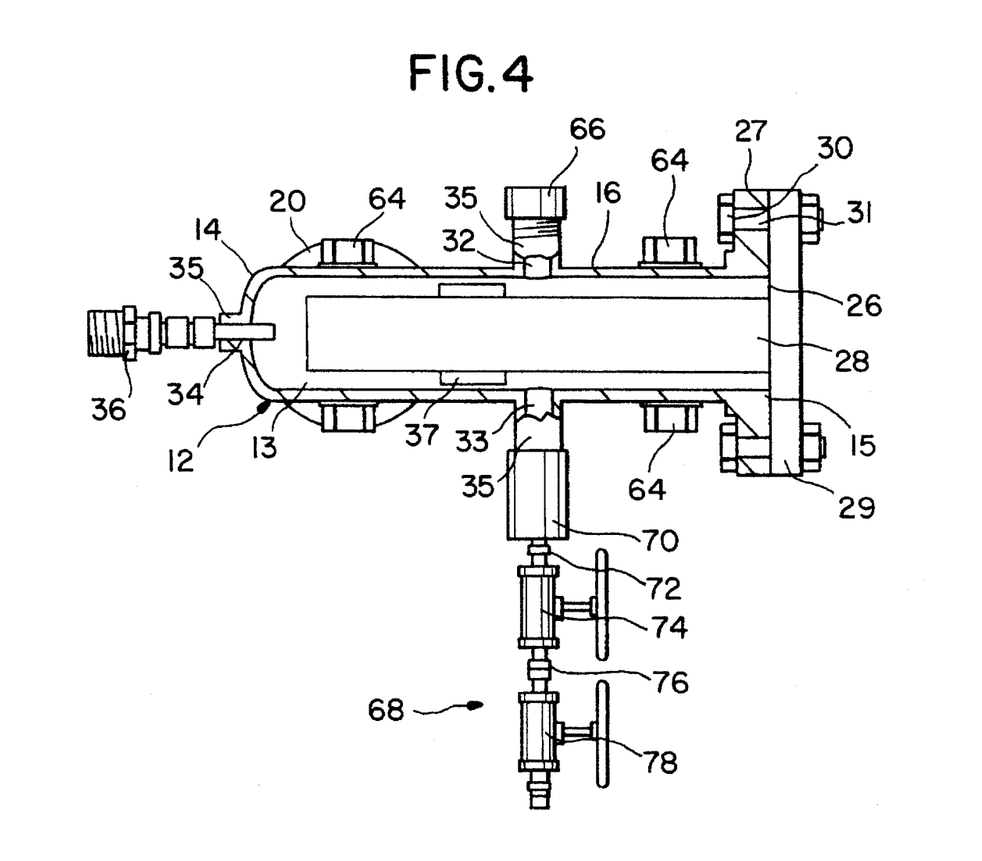
FIG. 4 is a partial sectional view of the canister substantially along line 4—4 of FIG. 3 but also showing a sampling assembly according to the invention.

A plug 28 is positioned within the canister 12 through the plug port 26 and partially occupies the internal volume 13 of the canister (as best illustrated in FIGS. 1 and 4). Although the plug port 26 could conceivably be located at any one of a number of locations on the canister 12, it is advantageously located in one of the ends. This arrangement facilitates the placement and removal of the plug 28 as may be required from time to time during the operation of the simulator 10. As will be more fully discussed below, in the preferred embodiment, the plug 28 is removably mounted on the canister 12 by means of flanges 27, 29.

Figure 5:
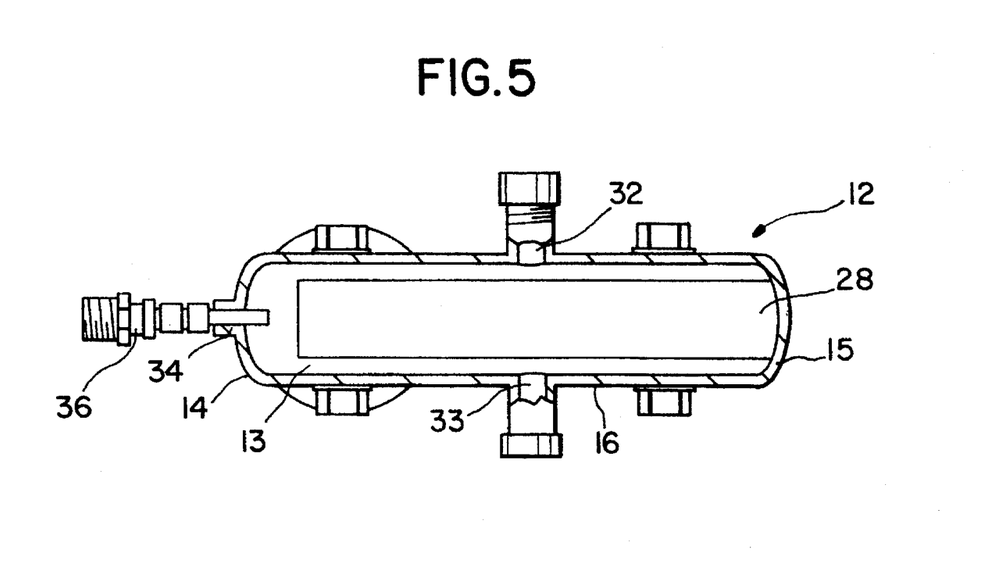
FIG. 5 is a partial sectional view of a modular canister according to an alternative embodiment of the invention, in which the plug is not removable.

In an alternative arrangement, the plug 28 may be permanently positioned within the canister 12, as is illustrated in FIG. 5. In this arrangement the plug 28 will be mounted in the canister 12 during fabrication of the canister 12 and will not be removable. All of the parameters relating to the plug configuration discussed below, including size, shape, and resistance to corrosion, apply equally where the plug is permanently mounted in the canister 12.

As discussed above, one of the critical parameters in simulating the corrosion activity of a high temperature liquid stream is the velocity of the stream within the process machinery and transport lines. Moreover, the velocity of a liquid stream flowing through a closed vessel can be calculated by dividing the flow rate of the liquid by the cross sectional area of the vessel. The relationship between the internal volume 13 of the canister 12 and the size of the plug 28 positioned within the canister is determined by this principle. By selecting a plug 28 having a suitable volume, the effective velocity of the liquid stream flowing through the canister 12 can be selected and controlled, assuming the flow rate of the stream is held constant. In addition, where several canisters 12a, 12b, 12c are coupled in series, plugs 28a, 28b, 28c having differing volumes can be advantageously selected and positioned within the canisters 12a, 12b, 12c to provide different velocities of the liquid stream in each of the canisters 12a, 12b, 12c in the series.

Figure 6:
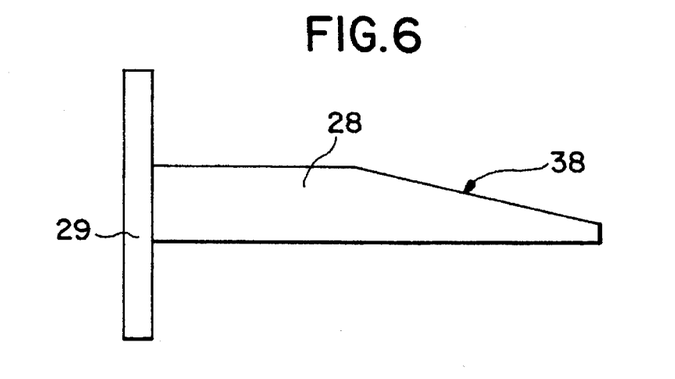
FIG. 6 is a top view of an alternative configuration of a plug according to the invention.
Figure 7:
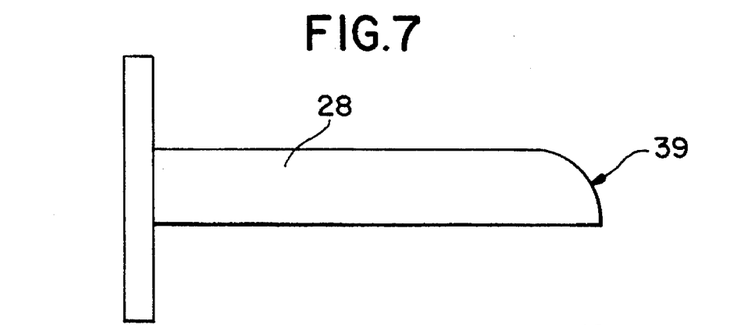
FIG. 7 shows another alternative plug configuration.

As has been mentioned, another flow characteristic important in the simulation of corrosion activity of high temperature liquids is impingement on the internal surfaces of machinery and lines. It is well known that fluid impingement forces are a function of fluid velocity and of the orientation of the impingement surface with respect to the impinging fluid stream. In application of this principle, the plug 28 can be advantageously provided with a surface geometry suitable to simulate a specific impingement surface orientation that might occur in process equipment. For example, the plug 28 could have an impingement surface oriented orthogonally with respect to the liquid stream flowing into the canister 12 through the inlet 18. Alternatively, the plug 28 could have an impingement surface 38 oriented at a predetermined angle with respect to the liquid stream, as illustrated in FIG. 6. In still another alternative, the plug could have an impingement surface 39 of predetermined planar or non-planar shape, as illustrated in FIG. 7. The geometry of the plug 28 may be subject to a number of other variations that might usefully model or simulate corrosion activity of a high temperature liquid stream by altering the flow characteristics of the stream. Where the simulator 10 includes a plurality of canisters 12a, 12b, 12c coupled in series, each of said canisters 12a, 12b, 12c could advantageously contain a respective plug 28a, 28b, 28c having a different geometry so as to simulate several different flow regimes in a single simulator 10.

In addition to altering flow characteristics by providing plugs 28a, 28b, 28c of different size and configuration, flow characteristics may be modified by altering the size or configuration of the inlet 18. As will be appreciated by those skilled in the art, the inlet 18 may thus function as an orifice, converting pressure head to velocity head where desirable. This may be accomplished by varying the size and configuration of the inlet 28 itself, or by the insertion of an orifice plate (not shown) upstream from the inlet 18 of the canister 12, or plurality of canisters 12a, 12b, 12c.

It will be appreciated that the material comprising the plug 28 may vary according to the type of simulation intended. In some applications, it may be desirable that the plug 28 itself undergo corrosion. In such cases, the plug 28 may be considered a corrosion measuring coupon and the plug 28 could be made of any material for which corrosion activity is to be simulated. This material would generally be any of the materials expected to be present in a particular industrial installation. In other applications, direct corrosion of the plug 28 may not be desirable. In such cases, the plug 28 is preferably made of a material that is sufficiently resistant to corrosion under the conditions present in the application. Depending upon the simulation intended, where a series of canisters 12a, 12b, 12c are coupled in series, the plugs 28a, 28b, 28c may be made of a variety of different materials in order to simulate corrosion activity on such materials.

Figure 8:
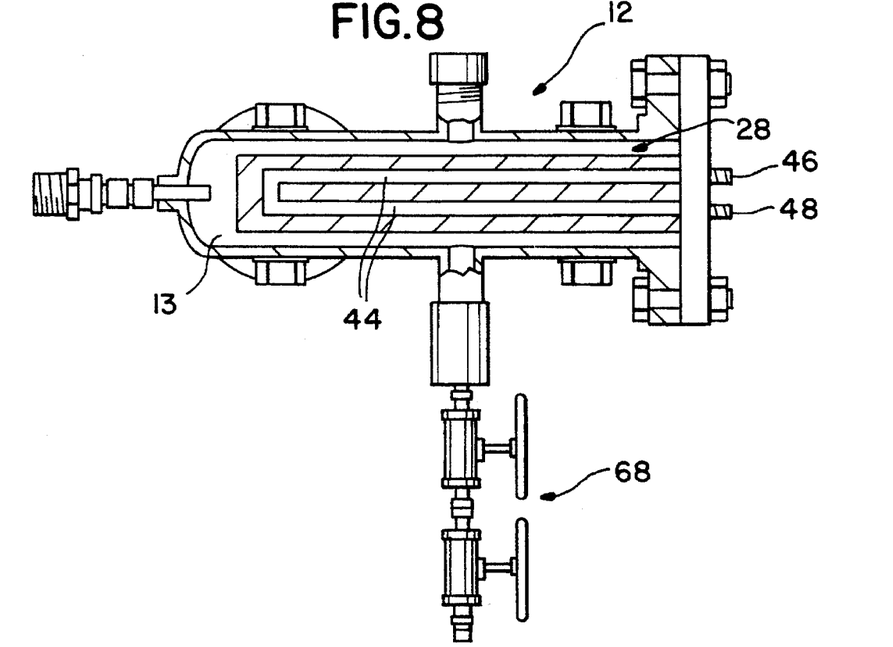
FIG. 8 is a partial sectional view of a canister and a plug according to the invention, illustrating an alternative plug configuration adapted to receive a coolant stream.

As illustrated in FIG. 8, the plug may comprise passages 44 for receiving and circulating a heat exchanging fluid. In this alternative embodiment, the plug 28 may be drilled to provide a circulation path as shown in FIG. 8, or may include similar heat exchanging arrangements as will be apparent to one skilled in the art. In operation, the plug shown in FIG. 8 receives a stream of heat exchanging fluid through the inlet 46. Heat exchanging fluid circulates through the passages 44 to selectively heat or cool the corrosive liquid stream flowing around the plug 28, and exits through the outlet 48. The inlet 46 and outlet 48 are preferably threaded fluid fittings as are commonly used in industrial installations. This alternative arrangement permits the temperature of the liquid stream to be altered as it progresses through a series of canisters, providing additional information on corrosion activity as a function of the liquid stream temperature. The heat exchanging fluid may be any fluid suitable for high temperature applications, such as Dowtherm.

As illustrated in FIG. 1, the corrosion simulator 10 receives a stream of high temperature corrosive liquid from a source 40 and discharges the liquid stream at a discharge point 42. In applications where corrosion activity in existing processes is to be monitored or simulated, the source of the liquid stream may be the actual process equipment, such as a distillation column in a petrochemical plant or oil refinery. The simulator 10 may be inserted in a pump around circuit through which a portion of the process liquid is diverted. In such applications, the discharge point 42 is generally a return line coupled to a point in the process equipment downstream from the source 40. In research applications, the source 40 of the liquid stream may be any holding tank or vessel (not shown) from which liquid is pumped and circulated through the simulator 10, and the discharge point 42 may be a return line connected to the holding tank where continuous circulation is desired, or any other discharge receiver where such circulation is not desirable. In either case, it is important that a sufficient pressure drop be established across the simulator to assure movement of corrosive liquid through the canister 12 or canisters 12a, 12b, 12c.

As illustrated in FIG. 1, the corrosion simulator 10 may advantageously include one or more of several elements coupled between the source 40 and the inlet 18 of the canister 12 or of the first in a series of canisters 12a, 12b. An inlet valve 50 permits the flow of liquid to the simulator 10 to be completely stopped when desired, for installation and subsequent servicing of the simulator 10. The inlet valve 50 may also be utilized for regulating the flow of corrosive liquid through the simulator 10. Such valves are commonly available in commerce and any suitable industrial quality valve may be used so long as it is compatible with the corrosive liquid being tested.

A heat exchanger 52 may be provided for heating and/or cooling the corrosive liquid stream. Such heating and cooling of the liquid stream may be desirable to maintain the prescribed simulation temperature where the temperature of the incoming liquid stream is cooler or hotter than the prescribed simulation temperature. Any suitable heat exchanger may be utilized, such as a shell-and-tube type exchanger. Due to the high temperature of the liquid stream passing through the simulator 10, a glycol-based or a silicone oil-based heat exchange medium will generally be preferred. In operation, the heat exchanger 52 would generally serve to heat the liquid stream to a desired elevated simulation temperature. Heat exchanging plugs 28, as discussed above, could then serve progressively to reduce or to raise the liquid stream temperature to generate a corrosion profile relating corrosion activity to liquid stream temperature. Alternatively, as will be readily apparent to one skilled in the art, where a number of canisters 12a, 12b, 12c are coupled in series, heat exchangers substantially similar to heat exchanger 52 may be inserted between each successive pair of canisters selectively to cool or to heat the liquid stream and to generate a corrosion profile or to maintain a constant temperature across the simulator 10.

A temperature detector 54 is advantageously included upstream from the inlet 18. This temperature detector 54 is preferably a thermocouple type and may function in conjunction with the heat exchanger 52 to control the temperature of the incoming corrosive liquid stream automatically. An injection line 56 may be connected to the incoming liquid stream piping at an injection point (represented diagrammatically by the reference numeral 57 in FIG. 1) and will generally include an injection valve 59. Such an injection line 56 is particularly useful in research applications where corrosion activity is to be simulated along with the effect of selected corrosion inhibitors. Corrosion inhibiting chemicals may be dosed through the injection line 56 directly into the liquid stream to determine their effect on limiting or mitigating the corrosion activity of the liquid stream. The injection line 56 may advantageously include a mixing device (not shown), such as a static mixer, to aid in distributing corrosion inhibitors in the liquid stream. As an alterative to the arrangement illustrated in FIG. 1, the simulator 10 may include injection lines 56 between some, or all, of the canisters 12a, 12b, 12c, where several canisters are coupled in series. This alternative arrangement may be particularly useful where simulation of the corrosive activity of the liquid stream is to include comparisons of corrosion activity of inhibitor treated liquid and untreated liquid.

Finally, a flow meter 58 may be provided to monitor the flow rate of corrosive liquid through the simulator 10. This flow meter 58 may be of any suitable type readily available for industrial use and may function in cooperation with the inlet valve 50 to control the flow of corrosive liquid through the simulator 10 and to maintain the flow at a desired constant rate. As an alterative to the arrangement illustrated in FIG. 1, the flow meter 58 may be located downstream from the simulator 10, between the simulator 10 and the discharge 42.

In a typical installation, the corrosion simulator 10 includes several modular canisters 12a, 12b, 12c coupled in series and mounted on a supporting rack 60 as depicted in FIG. 2. The supporting rack 60 may be situated at any convenient location, but is preferably located at an equipment level near the source 40 and discharge point 42 of the liquid stream to be tested. Support risers 62 are provided for rigidly mounting the canisters 12a, 12b, 12c on the supporting rack 60. As is more clearly depicted in FIGS. 3 and 4, mounting nuts 64 are preferably welded onto the external surface of the lateral wall 16 in order to facilitate mounting of the canisters 12a, 12b, 12c on the support risers 62. The canisters 12a, 12b, 12c are preferably heat treated after all such welding operations to relieve stresses the welding may have caused. These mounting nuts 64 are preferably provided on both the upper and lower surfaces of the lateral wall 16, as shown in FIG. 4. This arrangement offers the advantage of allowing the modular canister to be inverted for mounting. This feature is particularly useful where a number of canisters 12a, 12b, 12c are to be coupled in series and the entire series mounted on a supporting rack 60 as shown in FIG. 2.

Figure 3:
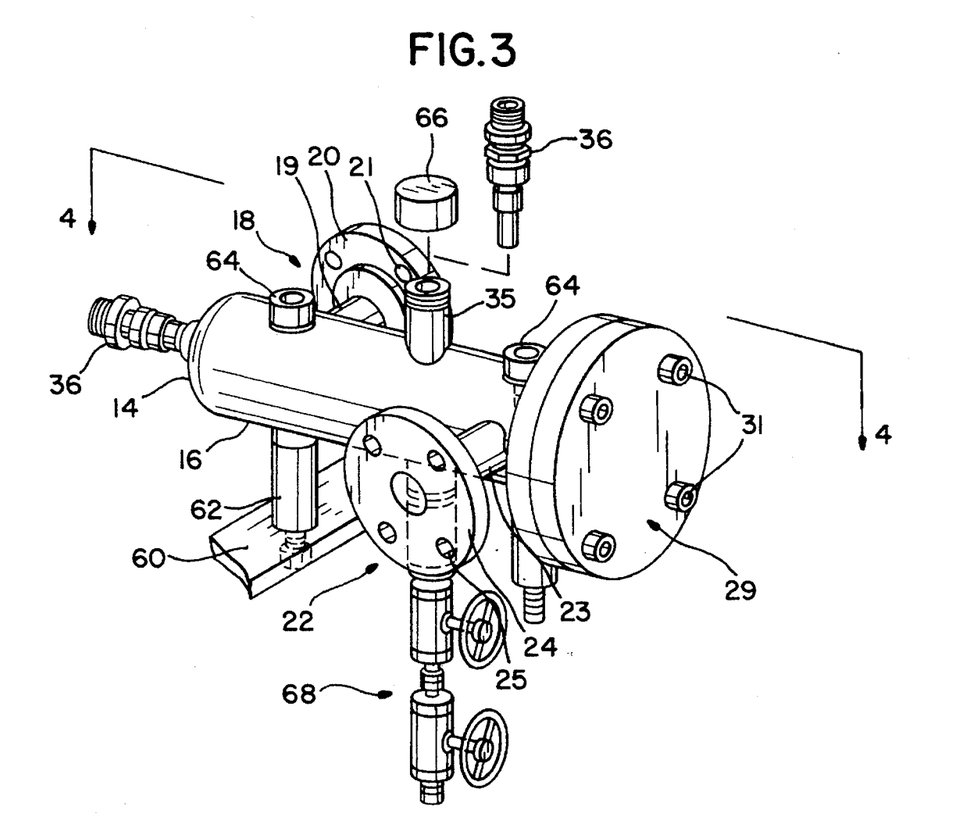
FIG. 3 is a perspective view of a single canister according to the invention illustrating the location of the inlet, the outlet, the plug, and several probes.

Turning more specifically now to the preferred embodiment of the canister 12 and plug 28, along with their related hardware, FIG. 3 shows a perspective view of a typical canister 12 in which a plug 28 has been removably positioned. As illustrated in FIG. 3, the canister 12 is substantially cylindrical in shape, having a blind first end 14 and a second end 15 joined by a lateral wall 16. The second end 15 is provided with a flanged plug port 26. A flanged inlet 18 and a flanged outlet 22 are also provided in the lateral wall 16. As depicted in FIGS. 3 and 4, the inlet 18 is located in the lateral wall 16 adjacent to the first end 14 and the outlet 22 is located on the opposing side of the canister adjacent to the second end 15.

It will be understood that where several canisters 12a, 12b, 12c are coupled in series, the inlet 18 of each successive canister operationally will be located alternatively adjacent to the first end 14 and the second end 15. The location of the inlet 18 and the outlet 22 adjacent to opposing ends of the canister 12 and on opposing sides of the lateral wall 16 is preferred. This arrangement forces the liquid stream received into the canister 12 through the inlet 18 to circulate through the canister 12 and around the plug 28 before exiting through the outlet 22.

As shown in FIG. 4, and as will be discussed more fully below, the canister 12 is preferably provided with several probe ports 32, 33, 34. An upper lateral probe port 32 and a lower lateral probe port 33 are advantageously situated near the midpoint of the lateral wall 16. An end probe port 34 may be advantageously provided in the blind end 14. In the preferred embodiment, the canister 12 is provided with upper and lower lateral probe ports 32, 33 and an end probe port 34. This arrangement offers considerable flexibility in positioning a number of probes 36 in the liquid stream to detect important simulation parameters including corrosion activity and temperature.

As can be seen in FIG. 4, the canister 12 is provided with lateral probe ports 32 and 33 and an end probe port 34. The probe ports 32, 33, 34 preferably include threaded weldolets 35 welded to and extending from the lateral wall 16 and end 14 of the canister 12. The weldolets 35 are typically 1 inch schedule 80 pipe, but other sizes and industrial ratings may be utilized depending on the particular simulation being performed. Probes 36 may be removably positioned in the probe ports so as to penetrate into the internal volume 13 of the canister 12. Such probes 36 may be corrosion detecting probes or temperature probes. Corrosion detecting probes are well known, and one form of such a probe is made by Rohrback Cosasco Systems, Incorporated and marketed under the tradename Corrosometer 2500 HT and Corrosometer 3500 HT. Temperature probes will typically be of the thermocouple type. Alternatively, combination probes may be utilized for measuring both temperature and corrosion activity at the same point. Moreover, the corrosion probes may be corrosion coupons as are well known. Surface corrosion coupons 37 may be placed within the canister at predetermined locations for monitoring and measuring corrosion activity at specific points in the liquid stream. Such coupons may be particularly useful for simulating the effects of impingement forces and local velocities on corrosion activity.

Judicious placement of the probes 36 may advantageously permit detection of particular velocity effects on corrosive activity. For instance, a corrosion detecting probe 36 may be located in a high velocity portion of the liquid stream, such as adjacent to the inlet 18. Another probe 36, located in a lower velocity portion of the liquid stream, such as in a lateral probe port 32, 33, may then be employed to detect corrosion activity under substantially similar conditions, with the exception of the local velocity. The difference in corrosion activity detected by the respective probes 36 may be correlated to the different velocities in which measurements were made.

The plug port 26 is preferably flanged. The mounting flange 27 is welded onto the end 15 of the canister and includes mounting bolt holes 30. The plug 20 terminates in a corresponding mounting flange 29 which mates with flange 27 when the plug is fully inserted into the canister. Bolts 31 hold the plug 28 securely in place within the canister 12 and assure a sufficient liquid seal between the canister flange 27 and the plug flange 29.

The inlet 18 and outlet 22 are preferably similarly flanged. In the case of the inlet 18 and outlet 22 however, pipe extensions 19 and 23 are welded to the lateral wall 16 of the canister and serve to locate the inlet and outlet flanges 20 and 24 at a convenient distance from the lateral wall. This arrangement facilitates coupling several canisters 12a, 12b, 12c in series while allowing sufficient clearance between canisters for the plug mounting flanges 27, 29. The inlet and outlet flanges 20, 24 are provided with bolt holes 21 and 25 respectively for receiving mounting bolts (not shown) during the installation of the canister 12 in a specific simulation application or during the coupling of several canisters 12a, 12b, 12c in series. The inlet and outlet flanges 20, 24 are machined or gasketed to assure a sufficient liquid seal when coupled to one another or to a source or discharge line.

When no probe in positioned in a particular probe port 32, 33, 34, that probe port is usually capped by means of a probe port cap 66. Such a cap 66 is shown in FIG. 4 mounted on the upper lateral probe port 32. In certain applications it may be desirable to extract samples of the corrosive liquid stream flowing through the simulator 10. For this purpose a sampling assembly 68 may be coupled to one of the probe ports 32, 33, 34. As illustrated in FIG. 4, the sampling assembly 68 is preferably coupled to the lower lateral probe port 33. A typical sampling assembly includes a reducing coupling 70 mounted onto the probe port 33 and a ball valve 74 coupled to the reducing coupling 70 by means of a close nipple 72. A second ball valve 78 is in turn coupled in series with the first ball valve 74 by means of a second close nipple 76. This arrangement permits a sample of the corrosive liquid stream to be captured between the ball valves by opening the first ball valve 74 with the second ball valve 78 in the closed position. The sample is then extracted by first shutting the first ball valve 74 and opening the second ball valve 78 to allow the sample to gravity drain into a suitable recipient (not shown). It is understood, of course, that other arrangements for extracting samples of the liquid stream can be employed satisfactorily.

We claim:

1. An apparatus for simulating corrosion activity of a high temperature liquid, comprising:
   a substantially cylindrical canister having an inlet for receiving a stream of a high temperature corrosive liquid from a source, an outlet for discharging said liquid, and a predetermined internal volume,
   a plug port positioned in said canister,
   a plug removably positioned within said canister through said plug port, said plug partially occupying the internal volume of said canister to alter flow characteristics of said stream of liquid,
   at least one corrosion probe access port positioned in said canister, and
   at least one corrosion probe removably positioned within said canister through at least one probe access port.

2. The apparatus as set forth in claim 1, wherein corrosion probe is a combination corrosion and temperature probe.

3. The apparatus as set forth in claim 1, further comprising a heat exchanger coupled between said source and said inlet for selectively altering the temperature of said stream of liquid.

4. The apparatus as set forth in claim 1, further comprising an injector coupled between said source and said inlet for injecting a corrosion inhibitor into said liquid stream.

5. The apparatus as set forth claim 1, further comprising a flow meter for monitoring the flow rate of liquid stream through said canister.

6. The apparatus as set forth in claim 5, wherein said flow meter is coupled between said source and said inlet.

7. The apparatus as set forth in claim 1, wherein portions of said canister wetted by said high temperature corrosive liquid are made of a corrosion resistant metal.

8. The apparatus as set forth in claim 7, wherein portions of said canister wetted by said liquid are made of a metal having at least a 3% molybdenum content.

9. An apparatus for simulating corrosion activity of a high temperature liquid, comprising:
   a modular canister having a first end, a second end, a substantially cylindrical lateral wall between said first and second ends, and a predetermined volume, said canister further comprising an inlet located in said lateral wall adjacent to said first end for receiving a stream of high temperature corrosive liquid from a source, an outlet located in said lateral wall adjacent to said second end for discharging said liquid stream, a plug port, a probe port communicating with said internal volume,
   a plug removably positioned in said plug port, said plug partially occupying the internal volume of said canister to alter flow characteristics of said stream of liquid
   a corrosion probe removably positioned in said canister through at least one probe port.

10. The apparatus as set forth in claim 9, wherein said plug port is located in said first end adjacent to said inlet.

11. The apparatus as set forth in claim 9, wherein said plug port is located in said second end adjacent to said outlet port.

12. An apparatus for simulating corrosion activity of a high temperature liquid, comprising:
   a plurality of serially coupled modular canisters, each of said canisters having an inlet for receiving a stream of high temperature corrosive liquid, an outlet for discharging said liquid, a plug port, and a predetermined internal volume,
   a plurality of plugs, one of said plugs being positioned within each of said canisters through said plug port, each of said plugs having a predetermined volume and partially occupying the internal volume of the respective canister to alter flow characteristics of said stream of liquid,
   a plurality of probe ports, one of said ports being positioned within each of said canisters, and
   a plurality of corrosion probes, one of said probes being removably positioned through each of said probe ports into each of said canisters,
the inlet of the first canister of said serially coupled canisters being coupled to a source of high temperature corrosive liquid, and the outlet of the last canister of said serially coupled canisters being coupled to a liquid discharge point such that a sufficient pressure drop is established across said apparatus to assure movement of corrosive liquid through said canisters.

13. The apparatus as set forth in claim 12, wherein the volume of at least one of said plugs is greater than the volume of at least one other of said plugs.

14. The apparatus as set forth in claim 12, wherein the shape of at least one of said plugs is different from the shape of at least one other of said plugs.

15. An apparatus for monitoring the corrosion activity of a high temperature corrosive liquid flowing through a liquid line, said apparatus comprising:

a plurality of serially coupled modular canisters, each of said canisters having an inlet for receiving a stream of high temperature corrosive liquid, an outlet for discharging said liquid, a plug port, a probe port, and a predetermined internal volume, and a plurality of plugs, one of said plugs being positioned within each of said canisters through said plug port, each of said plugs having a predetermined volume and partially occupying the internal volume of the respective canister to alter flow characteristics of said stream, a plurality of corrosion probes, one of said probes being positioned within each of said canisters through said probe port, the inlet of the first canister of said serially coupled canisters being coupled to said liquid line, and the outlet of the last canister of said serially coupled canisters being coupled to a liquid discharge point such that a sufficient pressure drop is established across said apparatus to assure movement of corrosive liquid through said canisters.

* * * * *